(12) United States Patent
Poquet et al.

(10) Patent No.: US 8,354,272 B2
(45) Date of Patent: Jan. 15, 2013

(54) ZINC-REGULATED PROKARYOTIC EXPRESSION CASSETTES

(75) Inventors: Isabelle Poquet, Paris (FR); Daniel Llull, Massy (FR)

(73) Assignee: Institut National de la Recherche Agronomique, Paris (FR)

( * ) Notice: Subject to any disclaimer, the term of this patent is extended or adjusted under 35 U.S.C. 154(b) by 1099 days.

(21) Appl. No.: 10/525,449

(22) Filed: Nov. 9, 2005

(65) Prior Publication Data

US 2006/0199246 A1    Sep. 7, 2006

Related U.S. Application Data

(63) Continuation of application No. PCT/FR03/02606, filed on Aug. 29, 2003.

(30) Foreign Application Priority Data

Aug. 30, 2002 (FR) ..................... 02 10805

(51) Int. Cl.
*C12N 15/00* (2006.01)
*C12N 15/09* (2006.01)
*C12N 15/11* (2006.01)
*C12N 15/31* (2006.01)

(52) U.S. Cl. .................. 435/320.1; 536/23.1; 536/24.1; 435/69.1; 435/71.2; 435/252.9; 435/252.35

(58) Field of Classification Search ........................ None
See application file for complete search history.

(56) References Cited

PUBLICATIONS

NCBI, LLU95834, *Lactococcus lactis* putative lipoprotein Nlp3 precursor gene, Apr. 24, 1998.*

"*Lactococcus lactis* putative lipoprotein Nlp3 precursor," Database EMBL 'en ligne! Apr. 15, 1998 , Poquet I. et al., Database accession No. U95834.

"Controlled Production of Stable Heterologous Proteins in *Lactococcus lactis*," Miyoshi A. et al., Applied Environmental Microbiology, vol. 68, No. 6, Jun. 2002, pp. 3141-3146.

An Export-Specific Reporter Designed for Gram-Positive Bacteria: Application to *Lactococcus lactis*, Poquet I. et al., Journal of Bacteriology, vol. 180, No. 7, Apr. 1998, pp. 1904-1912.

The Complete Genome Sequence of the Lactic Acid Bacterium *Lactococcus lactis*, Genome Research, vol. 11, No. 5, May 2001, pp. 731-753.

* cited by examiner

*Primary Examiner* — Maria Marvich
(74) *Attorney, Agent, or Firm* — William E. Beaumont

(57) ABSTRACT

An expression cassette comprising:
a) a bacterial promoter, $p_{Zn}$, containing a binding site for the *Lactococcus lactis* ZitR protein, which site comprises the following sequence:

AAAAATAANGTNNNNNNNNTTGACATTATTTTT,   (SEQ ID NO: 1)

in which TTGACA is the −35 box of said promoter, and N represents A, C, G or T;
b) a sequence encoding a polypeptide with at least 80% identity with the *Lactococcus lactis* ZitR protein, placed under the transcriptional control of said promoter; and wherein the polypeptide is obtained from *Lactococcus*; and
c) at least one restriction site allowing the insertion of a nucleotide sequence of interest under the transcriptional control of said promoter, and wherein the expression cassette does not comprise any part of the sequence encoding the *L. lactis* ZitS protein.

11 Claims, 9 Drawing Sheets

```
7371  cacaggaaac agctatgacc atgattacgc caagctcgaa attaaccctc actaaaggga acaaaagctg ggtaccgggc cccccctcga ggtcgacggt atcgatagcc
7481  cgcctaatga gcggcttt tttttgatatc gaattaccg ggaattcaga tcttgatca aggatctgtc agctggttca actagcggtg gtcaaactgt tagtaataaa
      ──────────→
       OLIGO 9
7591  acttattgtt ttgatgttcg gcttaaggat ggaaggattt ttcaaataaa aagtaaaaa ataatgttaa ctgg[tgaca] ttattttac tttgcta[tat aat]taaccag
7701  ta aactaatt at[ggagga]ca aatactatg antttagcaa atcaaatcga ccagtttctt gggcaatta tgcagtttgc anaaaacaag catgaaatat tactcggcga
        >>.........                                                                  .....zitR
7811  atgcnaaagt aatgttaagc taacaagcac gcaagaacat atcttaatga ttctagctgc agaggtttcg acaaacgcga gaattgccga gcaactcaag atttgccag
      >..........  .........  .........  .........  .........  .........  .........  .........  .........  .........zitR
7921  cagcggtaac taaagctctc aaaaaattac aagagcaaga actgattaaa tcaagtcggg caacaaatga cgaacgcgta gtcctttgaa gcctgacaga aaaagcaatt
      >..........  .........  .........  .........  .........  .........  .........  .........  .........  .........zitR
8031  ccagttgcta aagaacatgc tgctcatcat gagaaactc taagtaccta ccaagaatta ggagacaaat ttactgacga agaacaaaaa gtgataagtc aattcttatc
      >..........  .........  .........  .........  .........  .........  .........  .........  .........  .........zitR
8141  agtacttac[g gagagt]ttc gat gaagaaa atattgatgt tatttgctat tctacttcttg tccggcagtt ttacttcttg ctggttgtca aaaaacagca gacaaaccag aagttgtgac
      >.........  .........  ..zitR
             ←──────────
              OLIGO MUT
8251  aacttttgag ccgatgtatg aatttacgaa agcgattgtt ggagataagg ttaaaattga aaatattgtt ccggcgaatc aagaagttca cgaattttgaa ccgagtgcca
      >..........  .........  .........  .........  .........  .........  .........  .........  .........  .........zitS
8361  ttacgaaaaa aatgtagaa aatgcaaaga aaattgaagt cgagtttgac aaaggtcaaa gaactgataa atatgacgt ggcttagcgt atatttatgc tgatgaaaaa
      >..........  .........  .........  .........  .........  .........  .........  .........  .........  .........zitS
```

FIG. 2

SEQUENCE LISTING

```
<160> NUMBER OF SEQ ID NOS: 17

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      consensus sequence of the pzn bacterial promoter
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(18)
<223> OTHER INFORMATION: a, c, t, g, unknown or other
<220> FEATURE:
<221> NAME/KEY: -35_signal
<222> LOCATION: (19)..(24)

<400> SEQUENCE: 1
aaaaataang tnnnnnnntt gacattattt tt                                    32

<210> SEQ ID NO 2
<211> LENGTH: 47
<212> TYPE: DNA
<213> ORGANISM: Artificial Sequence
<220> FEATURE:
<223> OTHER INFORMATION: Description of Artificial Sequence: Synthetic
      consensus sequence of the pzn bacterial promoter
<220> FEATURE:
<221> NAME/KEY: modified_base
<222> LOCATION: (9)..(9)
<223> OTHER INFORMATION: a, c, t, g, unknown or other
<220> FEATURE:
<221> NAME/KEY: modified_base
<222> LOCATION: (12)..(18)
<223> OTHER INFORMATION: a, c, t, g, unknown or other
<220> FEATURE:
<221> NAME/KEY: -35_signal
<222> LOCATION: (19)..(24)
<220> FEATURE:
<221> NAME/KEY: modified_base
<222> LOCATION: (33)..(41)
<223> OTHER INFORMATION: a, c, t, g, unknown or other
<220> FEATURE:
<221> NAME/KEY: -10_signal
<222> LOCATION: (42)..(47)

<400> SEQUENCE: 2
```

```
aaaaataaang tnnnnnnntt gacattattt ttnnnnnnnn ntataat              47

<210> SEQ ID NO 3
<211> LENGTH: 32
<212> TYPE: DNA
<213> ORGANISM: Lactococcus lactis
<220> FEATURE:
<221> NAME/KEY: -35_signal
<222> LOCATION: (19)..(24)

<400> SEQUENCE: 3
aaaaataayg ttaactggtt gacattattt tt                               32

<210> SEQ ID NO 4
<211> LENGTH: 56
<212> TYPE: DNA
<213> ORGANISM: Lactococcus lactis
<220> FEATURE:
<221> NAME/KEY: -35_signal
<222> LOCATION: (19)..(24)
<220> FEATURE:
<221> NAME/KEY: -10_signal
<222> LOCATION: (42)..(47)

<400> SEQUENCE: 4
aaaaataatg ttaactggtt gacattattt ttactttgct atataattaa ccagta     56

<210> SEQ ID NO 5
<211> LENGTH: 57
<212> TYPE: DNA
<213> ORGANISM: Lactococcus lactis
<220> FEATURE:
<221> NAME/KEY: -35_signal
<222> LOCATION: (20)..(25)
<220> FEATURE:
<221> NAME/KEY: -10_signal
<222> LOCATION: (43)..(48)

<400> SEQUENCE: 5
aaaaaataac gttaactggt tgacattatt ttttctttgc tatataatta accagta    57

<210> SEQ ID NO 6
<211> LENGTH: 25
<212> TYPE: PRT
<213> ORGANISM: Lactococcus lactis

<400> SEQUENCE: 6

Met Lys Lys Ile Asn Leu Ala Leu Leu Thr Leu Ala Thr Leu Met Gly
1               5                   10                  15

Val Ser Ser Thr Ala Val Val Phe Ala
            20                  25

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ctaatgagcg ggcttttt                                               18

<210> SEQ ID NO 8
<211> LENGTH: 35
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 8
gctctagagc gggatccttc atcgaaactc ttcag                                35

<210> SEQ ID NO 9
<211> LENGTH: 1100
<212> TYPE: DNA
<213> ORGANISM: Lactococcus lactis
<220> FEATURE:
<221> NAME/KEY: -35_signal
<222> LOCATION: (295)..(300)
<220> FEATURE:
<221> NAME/KEY: -10_signal
<222> LOCATION: (318)..(323)
<220> FEATURE:
<221> NAME/KEY: RBS
<222> LOCATION: (343)..(348)
<220> FEATURE:
<221> NAME/KEY: modified_base
<222> LOCATION: (362)..(362)
<223> OTHER INFORMATION: a, c, t, g, unknown or other
<220> FEATURE:
<221> NAME/KEY: modified_base
<222> LOCATION: (412)..(412)
<223> OTHER INFORMATION: a, c, t, g, unknown or other
<220> FEATURE:
<221> NAME/KEY: modified_base
<222> LOCATION: (445)..(445)
<223> OTHER INFORMATION: a, c, t, g, unknown or other
<220> FEATURE:
<221> NAME/KEY: RBS
<222> LOCATION: (780)..(786)

<400> SEQUENCE: 9
cacaggaaac agctatgacc atgattacgc caagctcgaa attaccctc actaaaggga      60 acaaaagctg gtaccgggc ccccctcga ggtcgacggt atcgatagcc cgcctaatga     120
gcgggctttt ttttgatatc gaattacccg ggaattcaga tctttgatca aggatctgtc    180
agctggttca actagcggtg gtcaaactgt tagtaataaa acttattgtt ttgatgttcg    240
gcttaaggat ggaaggattt ttcaaataaa aaagtaaaaa ataatgttaa ctggttgaca    300
ttatttttac tttgctatat aattaaccag taaactaatt atggaggaca aaatactatg    360
antttagcaa atcaaatcga ccagtttctt ggggcaatta tgcagtttgc anaaaacaag    420
catgaaatat tactcggcga atgcnaaagt aatgttaagc taacaagcac gcaagaacat    480
atcttaatga ttctagctgc agaggtttcg acaaacgcga gaattgccga gcaactcaag    540
atttcgccag cagcggtaac taaagctctc aaaaaattac aagagcaaga actgattaaa    600
tcaagtcggg caacaaatga cgaacgcgta gtcctttgga gcctgacaga aaagcaatt    660 ccagttgcta agaacatgc tgctcatcat gagaaaactc taagtaccta ccaagaatta    720
ggagacaaat ttactgacga agaacaaaaa gtgataagtc aattcttatc agtacttacg    780
gaggagtttc gatgaagaaa atattgatgt tatttgctat tccggcagtt ttacttcttg    840
ctggttgtca aaaacagca gacaaaccag aagttgtgac aacttttgag ccgatgtatg    900
aatttacgaa agcgattgtt ggagataagg ttaaaattga aatattgtt ccggcgaatc    960 aagaagttca cgaatttgaa ccgagtgcca ttacgaaaaa aatggtagaa atgcaaaga   1020 aaattgaagt cgagtttgac aaaggtcaaa gaactgataa atatggacgt ggcttagcgt   1080
atatttatgc tgatggaaaa                                              1100

<210> SEQ ID NO 10
<211> LENGTH: 160
```

```
<212> TYPE: DNA
<213> ORGANISM: Lactococcus lactis
<220> FEATURE:
<221> NAME/KEY: -35_signal
<222> LOCATION: (123)..(128)
<220> FEATURE:
<221> NAME/KEY: -10_signal
<222> LOCATION: (146)..(151)

<400> SEQUENCE: 10
gatctgtcag ctggttcaac tagcggtggt caaactgtta gtaataaaac ttattgtttt    60
gatgttcggc ttaaggatgg aaggattttt caaataaaaa agtaaaaaat aatgttaact   120
ggttgacatt atttttactt tgctatataa ttaaccagta                         160

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caggaaacag ctatgacc                                                  18

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttctaagga tccattaact taaggag                                        27

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
tttgtgatgc atatgcaaat acaacggctg ttg                                 33

<210> SEQ ID NO 14
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Met Lys Lys Ile Asn Leu Ala Leu Leu Thr Leu Ala Thr Leu Met Gly
1               5                   10                  15

Val Ser Ser Thr Ala Val Val Phe Ala Tyr Ala
            20                  25
```

```
<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgcggatcct ttgaaaggat attcctc                                              27

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cctacgtatt agaaatgaat gttaaagc                                             28

<210> SEQ ID NO 17
<211> LENGTH: 145
<212> TYPE: PRT
<213> ORGANISM: Lactococcus lactis

<400> SEQUENCE: 17

Met Ser Leu Ala Asn Gln Ile Asp Gln Phe Leu Gly Thr Ile Met Gln
1               5                   10                  15

Phe Ala Glu Asn Lys His Glu Ile Leu Leu Gly Lys Cys Glu Ser Asp
            20                  25                  30

Val Lys Leu Thr Ser Thr Gln Glu His Ile Leu Met Leu Leu Ala Glu
        35                  40                  45

Gln Ile Ser Thr Asn Ala Lys Ile Ala Glu Lys Leu Lys Ile Ser Pro
    50                  55                  60

Ala Ala Val Thr Lys Ala Leu Lys Lys Leu Gln Glu Gln Glu Leu Ile
65                  70                  75                  80

Lys Ser Ser Arg Ala Thr Asn Asp Glu Arg Val Val Leu Trp Ser Leu
                85                  90                  95

Thr Glu Lys Ala Val Pro Val Ala Lys Glu His Ala Thr His His Glu
            100                 105                 110

Lys Thr Leu Ser Thr Tyr Gln Glu Leu Gly Asn Lys Phe Thr Asp Glu
        115                 120                 125

Glu Gln Glu Val Ile Ser Lys Phe Leu Ser Ala Leu Thr Glu Glu Phe
    130                 135                 140

Gln
145
```

ZINC-REGULATED PROKARYOTIC EXPRESSION CASSETTES

CROSS REFERENCE TO RELATED APPLICATIONS

This is a continuation application of International Application PCT/FR2003/002606, with an International filing date of Aug. 29, 2003, the latter of which in turn claims priority from France No. 02 10805, having a filing date of Aug. 30, 2002.

STATEMENT REGARDING FEDERALLY SPONSORED RESEARCH OR DEVELOPMENT (Not Applicable)

THE NAMES OF THE PARTIES TO A JOINT RESEARCH AGREEMENT (Not Applicable)

BACKGROUND OF THE INVENTION (1) Field of the Invention

The invention relates to the production of heterologous proteins in gram-positive bacteria, in particular lactic acid bacteria.

(2) Description of the Background

Besides their conventional uses in the agrofoods industry, lactic acid bacteria are currently increasingly used as host cells for the production of heterologous proteins of interest. These proteins of interest can be very varied in nature, and it is therefore desirable to have as large a choice as possible of expression tools in order to be able to optimize the production thereof as a function of the specificities of each one of them.

In general, it is necessary to use strong promoters that make it possible to obtain a sufficient level of expression of the gene of interest. In certain cases, constitutive promoters can be used; in other cases (for example when the product of the gene of interest is toxic for the host bacterium or there is a risk of it interfering with the metabolism thereof), it is preferable to use inducible promoters that make it possible to initiate or to stop the expression at the desired time.

Although lactic acid bacteria have many genes whose transcription is regulated by various factors, at the current time, there is only a relatively restricted choice of inducible promoters that can be used in practice for constructing expression cassettes for genes of interest (for review, cf. D E VOS, Curr. Op. Microbial., 2, 289-295, 1999). In fact, this use requires not only that the promoters concerned can be regulated, but also that there exists a sufficient expression differential between the various induction states; ideally, the expression should reach a high level under induction conditions and should be able to be completely blocked under non-induction conditions. In addition, it is necessary to be able to readily control the factors involved in the regulation of these promoters.

In previous studies, aimed at identifying exported proteins from *L. lactis* (POQUET et al., J. Bacteriol., 180, 1904-1912, 1998), the inventors cloned, by fusion with the reporter gene $\Delta_{SP}$Nuc, a fragment of genomic DNA of the *L. lactis* strain MG1363, comprising a gene called, at the time, nlp3 (New LipoProtein 3), the product of which exhibits homologies with an *S. pneumoniae* protein involved in the transport of metals. The sequence of this fragment is available on GEN-BANK under the number U95834.

The inventors also observed that the nlp3 gene was negatively regulated by divalent metal cations, in particular $Zn^{2+}$ (POQUET et al. "Use of a new reporter tool to demonstrate metal regulation of nlp3, a gene putatively involved in metal uptake in *Lactococcus lactis*"; 6th Symposium on Lactic Acid Bacteria, Veldhoven, The Netherlands, Sep. 19-23, 1999).

Furthermore, in the context of the complete sequencing of the *L. lactis* IL1403 genome, the nlp3 gene, renamed zitS, was identified as a constituent of an operon, called zitRSQP (BOLOTIN et al., Antonie van Leeuwenhoek, 76, 27-76, 1999; BOLOTIN et al., Genome Res. 11, 731, 2001). By homology with known sequences, putative functions in zinc transport were attributed to the genes of this operon. Thus, the product of the zitP gene is thought to constitute the permease of the transport system, the products of the zitS gene and of the zitQ gene are thought to ensure, respectively, binding with the substrate and binding with ATP, and the product of the zitR gene, which exhibits homologies with the marR transcriptional repressor family, is thought to be involved in the regulation of zinc transport.

Up until this point, use of the zitRSQP operon regulatory system for controlling the expression of heterologous genes had not been envisioned. In fact, although a negative regulation may be initiated by the addition of zinc (POQUET et al., 1999, mentioned above), the basal level of expression observed in the absence of this negative regulation did not appear to be sufficient to allow satisfactory production of proteins of interest. In addition, it was not known whether the putative repressor ZitR was effectively involved in repression of the expression of this operon, or whether other regulators, in particular the pleiotropic flp regulators, described as being involved in the regulation of zinc transport in *L. lactis* (GOSTICK et al., Mol. Microbiol., 31, 1523-35, 1999; SCOTT et al., FEMS Microbiol. Lett., 192, 85-89, 2000), could also be involved, either as corepressors or, conversely, as possible activators.

BRIEF SUMMARY OF THE INVENTION

Accordingly, an expression cassette is provided which contains
a) a bacterial promoter, $p_{Zn}$, containing a binding site for the *Lactococcus lactis* ZitR protein, which site contains the following sequence: AAAAATAANGTNNNNNNNTTGA-CATTATTTTT (SEQ ID NO:1), in which TTGACA is the −35 box of the promoter, and N represents A, C, G or T,
b) a sequence encoding a polypeptide with at least 80% identity with the *Lactococcus lactis* ZitR protein; placed under the transcriptional control of the promoter; and wherein the polypeptide is obtained from *Lactococcus*; and
c) at least one restriction site allowing the insertion of a nucleotide sequence of interest under the transcriptional control of the promoter, and wherein the expression cassette does not contain any part of the sequence encoding the *L. lactis* ZitR protein.

BRIEF DESCRIPTION OF THE SEVERAL VIEWS OF THE DRAWINGS

FIG. 2 illustrates the sequence of the region of the plasmid pVE8020 on which amplification is performed.

DETAILED DESCRIPTION OF THE INVENTION

Figure 1:
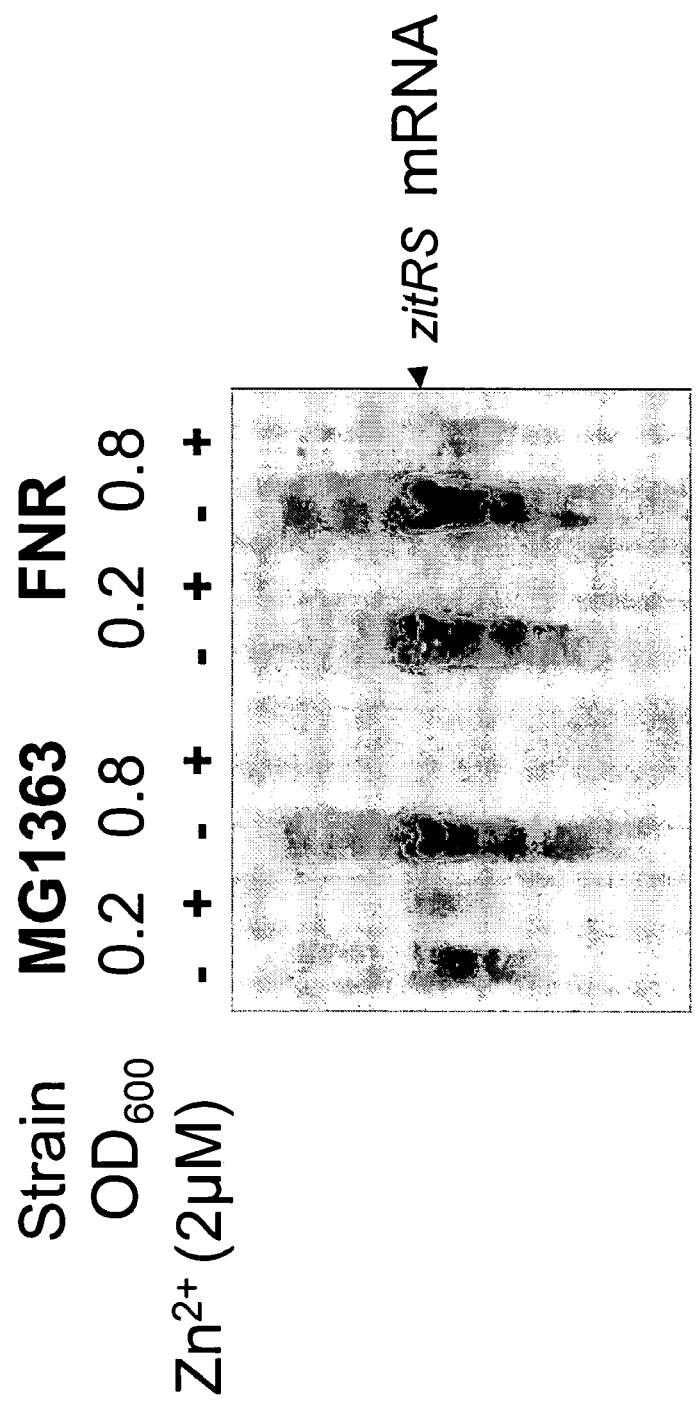
FIG. 1 illustrates the results of loading 60 μg of RNA onto a 1% agarose gel. After migration and transfer onto a nylon membrane, the zitRS transcripts are detected by Northern blotting with a probe specific for zitS gene.

Now, in continuing their studies on the regulation of the zitRSQP operon, the inventors noted, in the presence of very low concentrations of $Zn^{2+}$, a maximum level of expression that was much greater than could be assumed according to prior experiments, and which made it possible to attain an induction factor of greater than 100. In addition, they noted that the expression was independent of flp regulators, and could be entirely controlled by means of the ZitR protein.

Studying the structure of the *L. lactis* zitRSQP operon promoter has allowed the inventors to demonstrate, besides the elements conventionally present in bacterial promoters, namely the −35 (TTGACA) and −10 (TATAAT) boxes separated by 17 bp, a palindromic sequence overlapping the −35 box, which very probably represents the ZitR-binding site.

The observations reported above make it possible to assume that zitRSQP is regulated according to the following mechanism: the ZitR repressor can form, with intracellular $Zn^{2+}$, a complex exhibiting a very substantial affinity for the binding site over-lapping the −35 box; the ZitR-$Zn^{2+}$ complex bound to the palindrome prevents access of the RNA polymerase to the −35 box, and therefore represses the transcription; on the other hand, the non-complexed form of ZitR does not bind to the −35 site, allowing transcription of the operon, which is then carried out with great efficiency.

Regulation of the zitRSQP operon by means of ZitR therefore depends on the intracellular concentration of $Zn^{2+}$, which itself depends on the availability of $Zn^{2+}$ in the culture medium.

The zitRSQP operon very probably represents a very high affinity zinc transport system that is only used by the bacterium under very severe conditions of zinc deficiency, so as to allow cell survival; on the other hand, under the usual conditions of culturing on rich media, the zinc is abundantly present in the environment and is transported into the cell by systems with a lower affinity than the ZitSPQ complex, the synthesis of which is then repressed.

These properties of the *L. lactis* zitRSQP operon regulatory system demonstrated by the inventors make it possible to propose its use for the production of proteins of interest in host bacteria, especially gram-positive bacteria, and in particular lactic acid bacteria.

A subject of the present invention is the various aspects of this use.

According to a first variant, a subject of the present invention is an expression cassette consisting of:
- a bacterial promoter, hereinafter called $p_{Zn}$, containing a binding site for the *Lactococcus lactis* ZitR protein, which site comprises the following sequence:

AAAAATAANGTNNNNNNNNTTGACATTATTTTT, (SEQ ID NO: 1)

in which TTGACA represents the −35 box of said promoter, and N represents A, C, G or T;
- a sequence encoding a polypeptide exhibiting at least 80%, preferably at least 85%, and entirely preferably at least 95% identity with the *Lactococcus lactis* ZitR protein (GENBANK AAK06214), placed under the transcriptional control of said promoter;
- at least one restriction site allowing the insertion of a nucleotide sequence of interest under the transcriptional control of said promoter.

According to a preferred embodiment of the present invention, the $p_{Zn}$ promoter comprises the following sequence:

(SEQ ID NO: 2)
AAAAATAANGTNNNNNNNNTTGACATTATTTTTNNNNNNNNNNTATAAT in which TATAAT represents the −10 box of said promoter.

According to another preferred embodiment of the present invention, said $p_{Zn}$ promoter contains a binding site for the *Lactococcus lactis* ZitR protein comprising the following sequence:

AAAAATAAYGTTAACTGGTTGACATTATTTTT, (SEQ ID NO: 3)

in which Y represents T or C.

By way of example of $p_{Zn}$ promoters that can be used for constructing an expression cassette in accordance with the invention, mention will be made of:

the $p_{Zn}$ promoter of the *Lactococcus lactis* strain MG1363, which comprises the sequence:

AAAAATAATGTTAACTGGTTGACATTATTTTA (SEQ ID NO: 4)
CTTTGCTATATAATTAACCAGTA;

the $p_{Zn}$ promoter of the *Lactococcus lactis* strain IL1403, which comprises the sequence:

AAAAAATAACGTTAACTGGTTGACATTATTTTT (SEQ ID NO: 5)
TCTTTGCTATATAATTAACCAGTA.

According to a second variant, a subject of the present invention is an expression cassette consisting of:
- a bacterial promoter $p_{Zn}$, as defined above;
- at least one restriction site allowing the insertion of a nucleotide sequence of interest under the transcriptional control of said promoter.

A subject of the present invention is also expression cassettes resulting from the insertion of a nucleotide sequence of interest into an expression cassette in accordance with the first or with the second variant of the invention, under the transcriptional control of the $p_{Zn}$ promoter.

Said nucleotide sequence of interest may be any sequence that it is desired to express under the transcriptional control of the $p_{Zn}$ promoter. It may in particular be any sequence encoding a heterologous protein of interest that it is desired to produce in a host bacterium; said protein may, where appropriate, be a fusion protein, combining polypeptide sequences of diverse origin.

However, the expression cassettes in accordance with the first variant of the invention and comprising all or part of the sequence encoding the *L. lactis* ZitS protein, fused to a reporter gene, are excluded.

Expression cassettes in accordance with the invention may, where appropriate, also comprise the elements required for targeting the protein of interest to the cell surface, or for its secretion into the culture medium.

In this context, a subject of the present invention is expression cassettes resulting from the insertion of a nucleotide sequence encoding an extra-cellular targeting peptide, and of at least one restriction site allowing the cloning of a nucleotide sequence of interest as a translational fusion with said targeting peptide, under the transcriptional control of the $p_{Zn}$ promoter, into an expression cassette in accordance with the invention.

Said targeting peptide may, for example, be a secretion signal peptide, a transmembrane domain, a signal for anchoring to the wall, etc.

Many targeting peptides that can be used in the context of the present invention are known in themselves. By way of nonlimiting examples, mention will be made of the peptides described in the publication by POQUET et al. (1998, mentioned above), or in the publication by L E LOIR et al. (Appl. Environ. Microbiol., 67, 4119-4127, 2001).

For the production of secreted proteins, a preferred extracellular targeting peptide is the signal peptide of the *L. lactis* Exp4 protein, which corresponds to the sequence:

MKKINLALLTLATLMGVSSTAVVFA.          (SEQ ID NO: 6)

A subject of the present invention is also any recombinant vector comprising an insert consisting of an expression cassette in accordance with the invention.

A subject of the present invention is also gram-positive bacteria transformed with at least one expression cassette in accordance with the invention.

Preferably, they are lactic acid bacteria in particular lactococci, lactobacilli or streptococci that are thermophilic.

Where appropriate, they may be bacteria originating from bacterial strains comprising one or more modifications of their genome, aimed at improving the production and/or the secretion of proteins expressed in said bacteria, and/or at preventing their degradation. For example, in the context of the production of exported proteins, use may be made of a bacterial strain in which the PrtP protease activity and/or the HtrA protease activity are inactive, such as that described in PCT application WO 00/39309, or a bacterial strain that overproduces a protein that makes it possible to stabilize the exported proteins, such as the *Lactococcus lactis* Nlp4 protein or one of its homologs (POQUET et al. 1998, publication mentioned above).

A subject of the present invention is also the use of expression cassettes or of recombinant vectors in accordance with the invention, for producing proteins of interest in a gram-positive bacterium, in particular lactic acid bacteria.

The expression cassettes in accordance with the first variant of the invention can be used in a host bacterium, for controlling the time at which a gene of interest inserted into the cloning site is expressed, and the level of this expression.

When the host bacterium is cultured in the presence of an amount of zinc that is in excess with respect to its needs, the expression of the gene of interest is completely repressed. Depletion of $Zn^{2+}$ in the culture medium, which can be carried out simply by adding a divalent cation-chelating agent such as EDTA makes it possible to lift the repression, and to bring about expression of the gene. The level of expression can be readily regulated through the amount of chelating agent added.

The host bacterium can also be cultured in a medium comprising an amount of zinc that is just sufficient to cover its needs during a given period of the culture (for example during the growth phase). In this case, the depletion of zinc at the end of this period brings about expression of the gene of interest.

In this context, a subject of the present invention is a method for producing a protein of interest in a gram-positive bacterium, and in particular a lactic acid bacterium, characterized in that it comprises:

introducing into said bacterium an expression cassette in accordance with the first variant of the invention, comprising a sequence encoding said protein of interest;

culturing said bacterium in a medium containing an amount of $Zn^{2+}$ that is sufficient to repress the expression of said protein;

inducing the production of said protein by $Zn^{2+}$ depletion of said medium;

recovering the protein produced.

According to a preferred embodiment of the method in accordance with the invention, the $Zn^{2+}$ depletion of said medium is obtained by adding a divalent cation-chelating agent.

According to another preferred embodiment of the present invention, the $Zn^{2+}$ depletion of said medium is obtained by culturing the bacterium until depletion of the $Zn^{2+}$ initially present in the medium.

According to the experiments carried out by the inventors on the *L. lactis* model strain MG1363, an amount of $Zn^{2+}$ that is sufficient to repress the expression under the control of the $p_{Zn}$/ZitR system can be maintained throughout the duration of the culturing by using a medium containing, at the beginning of culturing, of the order of 1 to 2 µM of $Zn^{2+}$, it being possible for the total repression threshold to be estimated at between 100 nM and 1 µM of $Zn^{2+}$. The $Zn^{2+}$ concentration in the medium below which complete lifting of the repression of $p_{Zn}$ is obtained is very low (of nanomolar order, and at most a few nanomolar). The amount of divalent cation-chelating agent required in order to effect the $Zn^{2+}$ depletion and induce the expression under the control of the $p_{Zn}$ promoter varies according to the amount of $Zn^{2+}$ initially introduced into the culture medium; by way of indication, in the case of the MG1363 strain, for a rich culture medium such as M17 medium, a $Zn^{2+}$ depletion making it possible to induce maximum expression can be obtained using an EDTA concentration of the order of 0.1 mM; in SA medium, which contains 10 nM of $Zn^{2+}$, a $Zn^{2+}$ depletion making it possible to induce maximum expression can be obtained using an EDTA concentration of the order of 0.01 mM.

The amounts of $Zn^{2+}$ and of cation-chelating agent mentioned above are given by way of indication. Based on these indications, and on the other information provided by the description of the present invention, those skilled in the art can readily determine, by means of prior tests carried out, for example, by placing a reporter gene under the control of the $p_{Zn}$/ZitR system in an expression cassette in accordance with the invention, the most suitable amounts according to the bacterial species or strain concerned, the operating conditions used, such as the medium used, the methods of adding $Zn^{2+}$ and/or chelating agent (for example, all at once, in several steps, continuously, etc.), and the desired level of expression.

Expression cassettes in accordance with the second variant of the invention will preferably be used in strains of bacteria, in particular of lactococci, in which the endogenous ZitR repressor is inactive, along with, optionally, the ZitSPQ complex. Under these conditions, the $p_{Zn}$ promoter constitutes a strong promoter, allowing expression of the protein of interest throughout the duration of the culture. The inactivation of the ZitR receptor and of the ZitSPQ complex can be carried out in a manner known in itself, in particular by site-directed mutagenesis of the zitRSQP operon.

In this context, a subject of the present invention is a method for producing a protein of interest in a gram-positive bacterium in which the endogenous ZitR repressor is inactive, characterized in that it comprises:
- introducing into said bacterium an expression cassette in accordance with the second variant of the invention, comprising a sequence encoding said protein of interest;
- culturing said bacterium;
- recovering the protein produced.

The present invention can be implemented, for example:
- in the field of the production of heterologous proteins of therapeutic interest by genetic engineering, in order to have better control of the production of these proteins by the cultures of transformed bacteria;
- in the agrofoods industry, in particular in the production of fermented products, for controlling, according to the fermentation stage, the production of proteins of interest that make it possible in particular to influence the quality of the finished fermented product.

The present invention will be understood more thoroughly from the additional description which follows, which refers to nonlimiting examples illustrating the construction of expression cassettes in accordance with the invention.

Example 1

Regulation of ZIT by $Zn^{2+}$ in *L. lactis*

The expression of zit as a function of the concentration of $Zn^{2+}$ in the medium is measured by means of 2 different techniques:
- Measurement of the Nuc activity of the fusion ZitRS-$\Delta_{sp}$Nuc, carried by the plasmid pVE8020, in the *L. lactis* strain MG1363. The plasmid pVE8020 results from the cloning of the fragment of chromosomal DNA from the MG1363 strain corresponding to $p_{Zn}$zitRzitS' (GenBank U95834) in the plasmid pFUN (POQUET et al., 1998, mentioned above; GenBank AF038666).
- Quantification of the zitS mRNA in the wildtype MG1363 strain (endogenous expression of zitS) and in the MG1363 strain transformed with pVE8020.

Effect of Zinc on the Nuc Activity Under the Control of the $p_{Zn}$ Promoter

Two types of experiments were carried out:

1) The Nuc (*Staphylococcus aureus* nuclease) activity was measured on culture dishes containing chemically defined SA medium (Jensen and Hammer, *Appl. Env. Microbiol.* 59, 4363-66, 1993), which comprises a minimal amount of each of the elements required for bacterial growth, and is in particular low in zinc (10 nM of $ZnSO_4$).

A solution of $Zn^{2+}$ (20 µl of $ZnSO_4$ at 0.1 M) is deposited on this medium in the form of a streak crossing the dish.

After absorption of the $Zn^{2+}$ deposit, 2 deposits of bacteria are made in the form of 2 streaks that are parallel to one another and cut across the zinc streak such that they are perpendicular to it: a control deposit (MG1363 strain transformed with a plasmid (pVE8009) carrying the fusion Usp-$\Delta_{sp}$Nuc under the control of the Usp promoter) and a deposit of the MG1363 strain transformed with pVE8020 (MG1363 (pVE8020)).

Overnight incubation of the dishes at 30° C. allows growth of the bacteria and the creation of a gradient of decreasing $Zn^{2+}$ concentrations by diffusion from the streak of $ZnSO_4$.

A staining test for nuclease activity is carried out by depositing onto the dishes a detection overlayer containing toluidine blue, and incubating at 37° C. (LACHICA et al., *Appl. Microbiol.*, 21, 585-87, 1971; L E LOIR et al., *J. Bacteriol.*, 176, 5135-39, 1994): the Nuc activity is detected by the detection overlayer turning pink, forming a halo around the streaks of bacterial deposits.

While the halo observed around the streak corresponding to the control deposit is of constant size and intensity over the entire length of the bacterial streak (which indicates that neither the nuclease activity of Usp-$\Delta_{sp}$Nuc, nor its exportation, nor its expression, depend on $Zn^{2+}$), that observed around the streak corresponding to the MG1363(pVE8020) deposit is limited to the end furthest away from the zinc deposit, where its width and its intensity are comparable to those observed for the control deposit; the intensity decreases as it gets nearer to the zinc deposit, and no halo is observed in the region of the intersection with said zinc deposit.

It therefore appears that high concentrations of zinc repress the expression of the promoter of the zitRSQP operon.

2) The regulation was also studied by detection of the Nuc reporter on an SDS-PAGE gel by virtue of its enzymatic activity (zymogram). For this experiment, the SA medium was again zinc-depleted, either by omitting any addition of $ZnSO4$ during its preparation, or by adding 0.01 nM EDTA to it. The *L. lactis* strain MG1363(pVE8020) was inoculated into this medium, and the culture was then divided up into two portions, and 2 µM of $Zn^{2+}$ was added to only one of these portions. After growth at 30° C. without shaking overnight, culture samples were taken, standardizing their volume according to their $OD_{600}$ so as to obtain a number of cells equivalent to that of 1 ml of culture at $OD_{600}=1$. The samples were precipitated with concentrated trichloroacetic acid, washed, lyzed in the presence lysozyme and SDS, and taken up in a loading buffer, according to the protocol described in POQUET et al. (1998, mentioned above).

The proteins were then separated according to their molecular weight on an SDS-PAGE gel containing 12.5% of acrylamide. The Nuc activity was detected as described above. Three protein forms exhibiting nuclease activity (which, according to their molecular weight, correspond to the precursor with an uncleaved signal peptide, to the mature form Nlp3-$\Delta_{sp}$Nuc, and to the NucA degradation product) were detected only in the culture sample to which no addition was made. No protein having Nuc activity was detected in the sample supplemented with $Zn^{21}$. These results demonstrate that the repression is complete in the presence of 2 µM of $Zn^{2+}$.

Effect of EDTA on the Nuc Activity Under the Control of the $p_{Zn}$ Promoter

The Nuc activity is measured on culture dishes containing M17 medium (TERZAGHI and SANDINE, *Appl. Environ. Microbiol.*, 29, 807-13, 1975) rich in zinc.

A solution of EDTA (20 µl at 0.1 M) is deposited, as is the MG1363 strain containing the control plasmid, and the MG1363(pVE8020 strain), in the form of streaks, as described above.

After incubation at 30° C. overnight, the Nuc activity is detected as described above.

The halo observed around the streak corresponding to the control deposit is, like that observed in case of the zinc, of constant size and intensity over the entire length of the streak. On the other hand, surprisingly, that observed around the streak corresponding to the MG1363(pVE8020) deposit is, in the region of the EDTA deposit, much more intense than that of the control deposit; the intensity decreases very rapidly as the distance from this intersection increases.

It therefore appears that EDTA induces expression of the promoter of the zitRSQP operon. The level of expression also appears to be higher than that observed at a distance from the zinc streak in the preceding experiment, and also higher than that of the control, that is controlled by the Usp promoter: it is therefore possible to attain a very high level of induction of $p_{Zn}$ zitR by means of concentrations of EDTA which do not affect the bacterial growth (such as 0.1 mM in M17).

Quantitative Evaluation of the Effect of EDTA on the Nuc Activity Under the Control of the Ezn Promoter In order to quantitatively evaluate the effect of EDTA on the Nuc activity expressed under the control of the promoter of the zitRSQP operon, the following experiments were performed:

The MG1363 strain transformed with pVE8020 is cultured in M17 medium supplemented with 5 µg/l of erythromycin, until it reaches the exponential phase ($OD_{600}$=0.3) or the stationary phase ($OD_{600}$=1.2). This culture is divided up into 4 subcultures; EDTA is then added to 3 of them, at various final concentrations (3.3 mM; 0.33 mM; 0.033 mM); the fourth receives no addition of EDTA (0 mM EDTA). After incubation for 30 min or for 1 h 30 min, samples of each culture are taken. The number of cells of each sample is standardized by adjusting the volume so as to obtain a number of cells equivalent to that of 1 ml of culture at $OD_{600}$=1.

The cells are then lyzed and precipitated by means of treatment with concentrated (16.7%) trichloro-acetic acid, washed with acetone (80%) and taken up in 100 µl of Tris buffer (50 mM, pH 7). 10 µl of each sample thus treated are deposited on a dish containing medium for detecting the Nuc activity (LACHICA et al., 1971; L E LOIR et al., 1994, mentioned above). The Nuc activity is evaluated by means of the size of the halo and the intensity of the pink coloration around each deposit. For a quantitative evaluation of the level of activity, a standard range of purified Nuc protein is deposited on the same dish (4-fold serial dilution starting from 400 µg).

It is noted that the size of the halo and the intensity of the coloration varies according to the EDTA concentration which was used to treat the cells. In the absence of EDTA, a very thin halo without any clear coloration is observed; at 0.033 mM EDTA, a thin halo that is clearly colored pink is observed; at 0.33 mM, a broad halo with a very intense pink coloration is observed. No increase in the size or in the intensity of the halo is observed from 0.33 to 3.3 mM. No significant difference in the size and in the intensity of the halo is noted between the addition of EDTA carried out in the exponential phase and that carried out in the stationary phase, nor between the two incubation times (30 min or 1 h 30 min).

These results indicate that the level of induction of the expression of $p_{Zn}$ increases with the concentration of EDTA added, up to a saturation threshold (which is reached in M17 medium, under the experimental conditions described here, for an EDTA concentration of the order of 0.33 mM, whatever the growth phase and the incubation time).

Comparison with the standard range of purified Nuc protein makes it possible to estimate that the level of induction obtained by the addition of 0.33 mM of EDTA in M17 medium is of the order of 100.

Effect of Zinc on Transcription of the Zit Operon

The strains used are the *L. lactis* subsp *cremoris* wild-type strain MG1363, and its mutant derivative FNR (flpA flpB double mutant, SCOTT et al., 2000, mentioned above; GOSTICK et al., 1999, mentioned above). The flp genes are pleiotropic regulators involved in particular in zinc transport: in FNR, the intracellular zinc concentration is seven to eight times lower than that of the wild-type strain (GOSTICK et al., 1999, mentioned above).

Starting with an overnight preculture of each strain in SA medium supplemented, only for FNR, with 5 µg/µl of erythromycin and 5 µg/µl of tetracyclin, a culture is performed at 30° C. in SA medium (the $Zn^{2+}$ concentration of which is 10 nM). In the early exponential phase ($OD_{600}$ 0.07 to 0.08), this culture is divided up into two parts: one (+) has $ZnSO_4$ added to it, so as to obtain a final $Zn^{2+}$ concentration of 2 µM (which does not affect the growth); the other (−) receives no addition. The culture is continued without modification up until the exponential phase ($OD_{600}$=0.2) or stationary phase ($OD_{600}$=0.8). The bacterial RNA is then extracted according to the protocol described by RAYA et al., (*J. Bacteriol.*, 180, 3174-80, 1998).

After extraction, the RNA concentration is evaluated by measuring the OD260: 60 µg of RNA are loaded onto a 1% agarose gel. After migration and transfer onto a nylon membrane, the zitRS transcripts are detected by Northern blotting, with a probe specific for the zitS gene.

The results are given in FIG. 1.

These results show that a specific mRNA of the size expected for zitRS is observed only in the absence (−) of addition of $Zn^{2+}$, and never in its presence (+), whatever the strain and whatever the growth phase at the time of the addition.

This shows 1) that the repression, by $Zn^{2+}$, of the expression of the zit operon occurs at the transcriptional level, 2) that it is complete for a $Zn^{2+}$ concentration in the medium of 2 µM, and 3) that it is independent of the flp genes, since it is exerted in the FNR mutant. The latter point indicates that the regulation by $Zn^{2+}$ depends entirely on the zitR regulator.

In the absence of addition of $Zn^{2+}$, a very high level of expression is observed, except for the MG1363 strain in the exponential phase, where only a low expression is observed. These results indicate that, despite the very low concentration of $Zn^{2+}$ (10 nM) in the starting SA medium, the intracellular concentration of $Zn^{2+}$ at the time of the exponential phase when the sample was taken is still sufficient, in the case of the MG1363 strain, to strongly repress the transcription of the zit operon. On the other hand, in the stationary phase, after depletion of the $Zn^{2+}$ present in the medium, the expression is very strong. In the case of the FNR strain, the 10 nM concentration of $Zn^{2+}$ in the starting medium is insufficient to ensure, even during the exponential phase, an intracellular concentration of $Zn^{2+}$ that represses transcription of the zit operon.

It therefore appears that the induction of the expression depends directly on the intracellular concentration of $Zn^{2+}$, and that said concentration must be very low in order to obtain maximum expression.

This can be obtained in particular:

1) By decreasing the extracellular concentration of $Zn^{2+}$; this must in fact be much lower than 10 nM, where considerable repression is still observed compared with the maximum level of induction. The extracellular concentration of $Zn^{2+}$ can, for example, be decreased by adding a chelating agent such as EDTA (whatever the growth phase), or by operating in the stationary phase, under conditions where the $Zn^{2+}$ initially present in the medium has been consumed by the bacteria during growth, or by a combination of these two means.

2) By using mutants in which the zinc transport is affected, and which, as a result, have a very low intracellular $Zn^{2+}$ concentration, such as the FNR strain mentioned above.

Example 2

Construction of Expression Vectors Under the Control of the zitRSQP Operon Regulatory System Construction of Plasmids Containing the zitRSQP Operon Regulatory System
Plasmid pDI11

The $p_{Zn}$-zitR promoter-regulator system of the MG1363 strain is obtained by PCR amplification (DyNAzyme EXT kit from Finnzymes) of part of the $p_{Zn}$zitRzitS' insert (GenBank U95834) of the plasmid pVE8020, with the oligonucleotides oligo 9 and oligo MUT:

```
Oligo 9:                              (SEQ ID NO: 7)
5'-CTAATGAGCGGGCTTTTT-3'

Oligo MUT:                            (SEQ ID NO: 8)
5'-GCTCTAGAGCGGGATCCTTCATCGAAACTCTTCAG-3'
```

Oligo 9 hybridizes with the multiple cloning site (MCS) of pFUN, and makes it possible to amplify any insert cloned into this vector. Oligo MUT makes it possible to remove the potential zitS ribosome binding site (RBS) in order to facilitate the cloning of the PCR fragment: its sequence, located in the overlapping region between zitR and zitS, has two mutations (underlined) in the RBS (the wild-type sequence 5'-GGAGGAG-3' is mutated to 5'-TGAAGAG-3', complementary to 5'-CTCTTCA-3' in oligo MUT), and the two restriction sites BamHI and XbaI (in bold).

The sequence of the region of the plasmid pVE8020 on which the amplification is performed (SEQ ID NO: 9) is represented in FIG. 2. The numbers to the left of the sequence correspond to the numbering of the entire sequence of the plasmid pVE8020. The pairing regions for the primers oligo 9 and oligo MUT are represented in bold and with arrows. The sequences encoding ZitR and part of ZitS are indicated. The potential RBSs (ribosome binding sites) of zitR and zits are boxed, and the ATG translation initiator codons are underlined. The –35 and –10 boxes of the promoter are boxed and highlighted in gray; the potential transcription initiation site is indicated by a double underlining.

The 700 by amplification product is treated with the *Escherichia coli* DNA polymerase Klenow fragment (PolIK), and then with XbaI. This modified fragment is purified and cloned into the vector pFUN, digested beforehand with EcoRV and XbaI: the ligation mixture (fragment+pFUN+T4 phage ligase) is used to electroporate the *Lactococcus lactis* strain MG1363, and erythromycin-resistant clones are selected on M17 solid medium+0.5% glucose+5 μg/ml erythromycin. One of these clones, containing a recombinant plasmid of 8.2 kb, hereinafter called pDI11, is chosen.

Figure 3A:
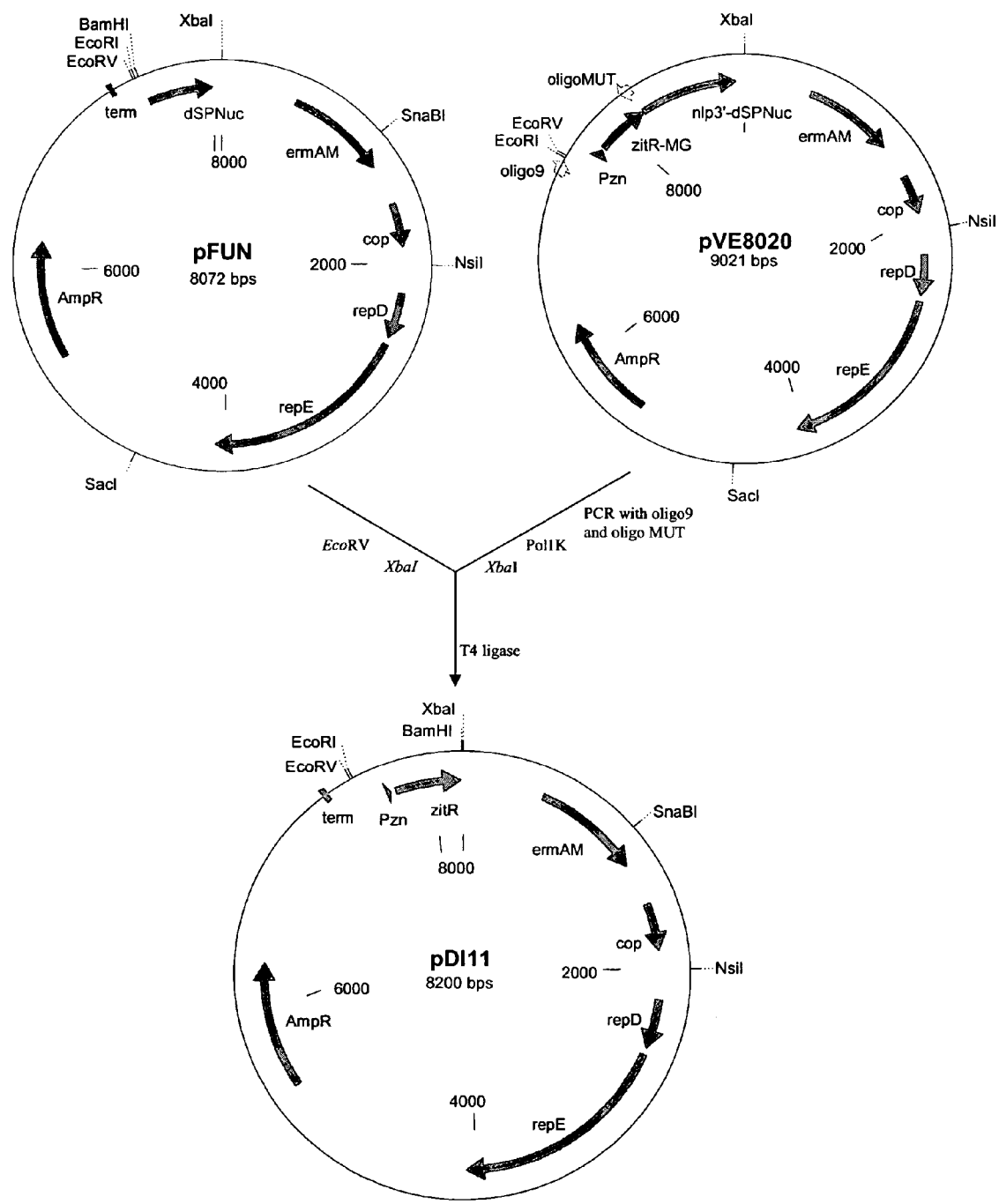
FIG. 3(a) illustrates the steps involved in constructing plasmid pDI11 from plasmid pFUN and pVE8020.

The steps for constructing this plasmid are represented in FIG. 3a.

It contains the entire sequence encoding ZitR, and also a 5' sequence comprising the $p_{Zn}$ promoter. This 5' sequence (SEQ ID NO:10) is represented hereinafter (up to the potential transcription initiation site):

```
GATCTGTCAGCTGGTTCAACTAGCGGTGGTCAAACTGTTAGTAATAAAAC

TTATTGTTTTGATGTTCGGCTTAAGGATGGAAGGATTTTTCAAATAAAAA
```

AGTAAAAAATAATGTTAACTGGTTGACATTATTTTTACTTTGCTATATAA

TTAACCAGTA.

Plasmid pDI12 pDI11 is digested with EcoRI and EcoRV and treated with PolIK so as to obtain a linear fragment of 8.18 kb lacking the restriction sites of the MCS of pFUN (which makes it possible to introduce them subsequently, elsewhere in the construct), and then treated with the T4 phage ligase. The MG1363 strain is electroporated with the ligation mixture, and an erythromycin-resistant clone containing the plasmid pDI12 is selected as described above.

Figure 3B:
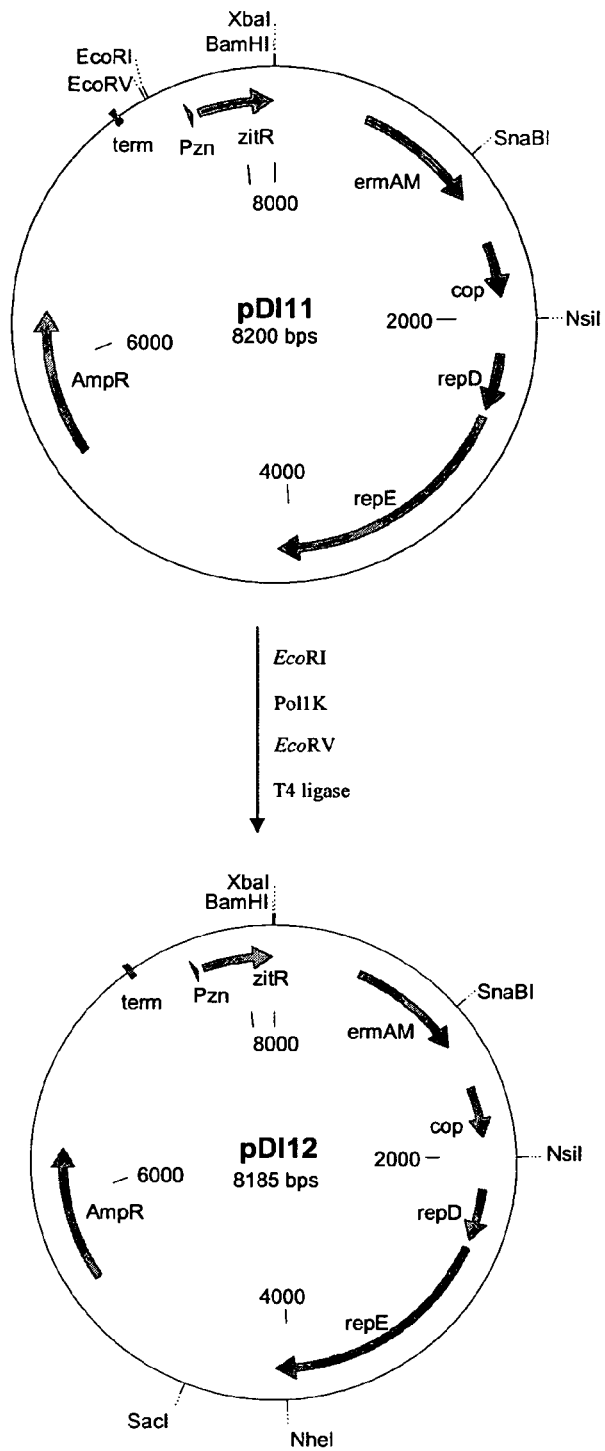
FIG. 3(b) illustrates the steps involved in constructing plasmid pDI12 from plasmid pDI11.

The steps for constructing this plasmid are represented in FIG. 3b.

Construction of Plasmids Containing a Reporter Gene Under the Control of the zitRSQP Operon Regulatory System
Plasmid pDI24 pDI24 comprises the following elements: a sequence encoding a reporter protein for testing the system, followed by a terminator.

The chosen reporter protein is NucB, the form lacking a signal peptide of the Nuc nuclease from *Staphylococcus aureus* (SHORTLE, Gene, 22, 181-189, 1983). Its open reading frame is cloned into the plasmid pSEC1 (or pVE3684, CHATEL et al., *Clin. Diagn. Lab. Immunol.*, 8, 545-551, 2001) under the control of the $p_{nis}$ (nisin-inducible) promoter for transcription, and $Usp_{45}$ signals from *L. lactis* for translation ($RBSusp45$ and initiation codon) and secretion (PSUsp45 signal peptide): the entire assembly $p_{nis}$-RBSUsp45-PSUsp45 is cloned into pDI24.

The terminator selected is the T1T2 terminator (PESCHKE et al., *J. Mol. Biol.*, 186, 547-555, 1985) which originates from the plasmid pVE5239 (DIEYE et al., *J. Bacterial.*, 183, 4157-4166, 2001).

To construct pDI24, pSEC1 is digested with XhoI, treated with T4 phage DNA polymerase, and digested with ClaI, so as to obtain a linear form of 3.8 kb. In parallel, pVE5239 is digested with SacI, treated with T4 phage DNA polymerase, and digested with ClaI, so as to obtain a 217 by fragment containing the T1T2 terminator. This fragment is purified and ligated with the linear form of the vector pSEC1, and the ligation mixture is used to transform the *E. coli* strain TG1. Chloramphenicol resistant clones are selected on LBT+12.5 μg/ml chloramphcnicol dishes. One of these clones, containing a 4 kb plasmid called pD124, is selected.

Figure 4:
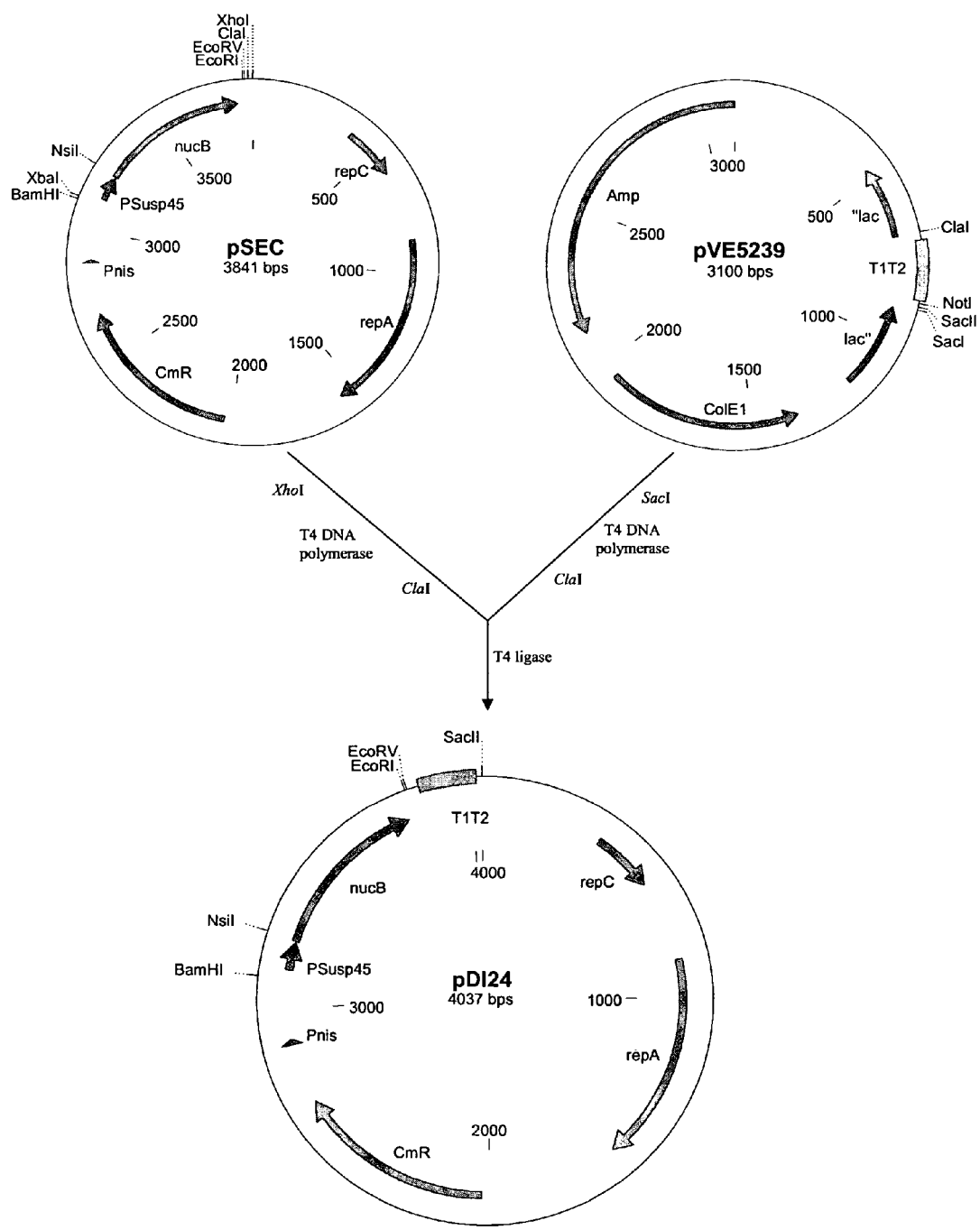
FIG. 4 illustrates the steps involved in constructing plasmid pDI24 from plasmids pSEQ and pVE5239.

The steps for constructing pDI24 are represented in FIG. 4.
Plasmid pDI1224

The fusion PSUsp45-NucB is placed under the 10 control of the $p_{Zn}$-zitR expression system in the plasmid pDI12, so as to produce the plasmid pDI1224.

pDI12 is digested with XbaI, treated with T4 phage DNA polymerase, and then digested with BamHI, so as to obtain a linear form of 8.1 kb. In parallel, pDI24 is digested with SacII, treated with T4 phage DNA polymerase, and digested with BamHI, so as to obtain a 932 bp fragment containing the open reading frame of the NucB reporter protein (under the control of RBSUsp45 and of PSUsp45), and the transcription terminator T1T2. This 932 bp fragment is purified and ligated with the linear form of the vector pDI12, and the ligation product is used to transform MG1363. The transformants are selected on solid M17 medium+0.5% glucose+5 μg/ml erythromycin+0.2 mM EDTA. The EDTA makes it possible to induce, by means of the $p_{Zn}$-zitR system, the expression of the reporter and therefore to perform a first screening of the Nuc+ phenotype of the recombinant clones. The Nuc activity assay is carried out according to the protocol described by L E LOIR et al., (*J. Bacteriol.* 176, 5135-5139, 1994).

Figure 5:
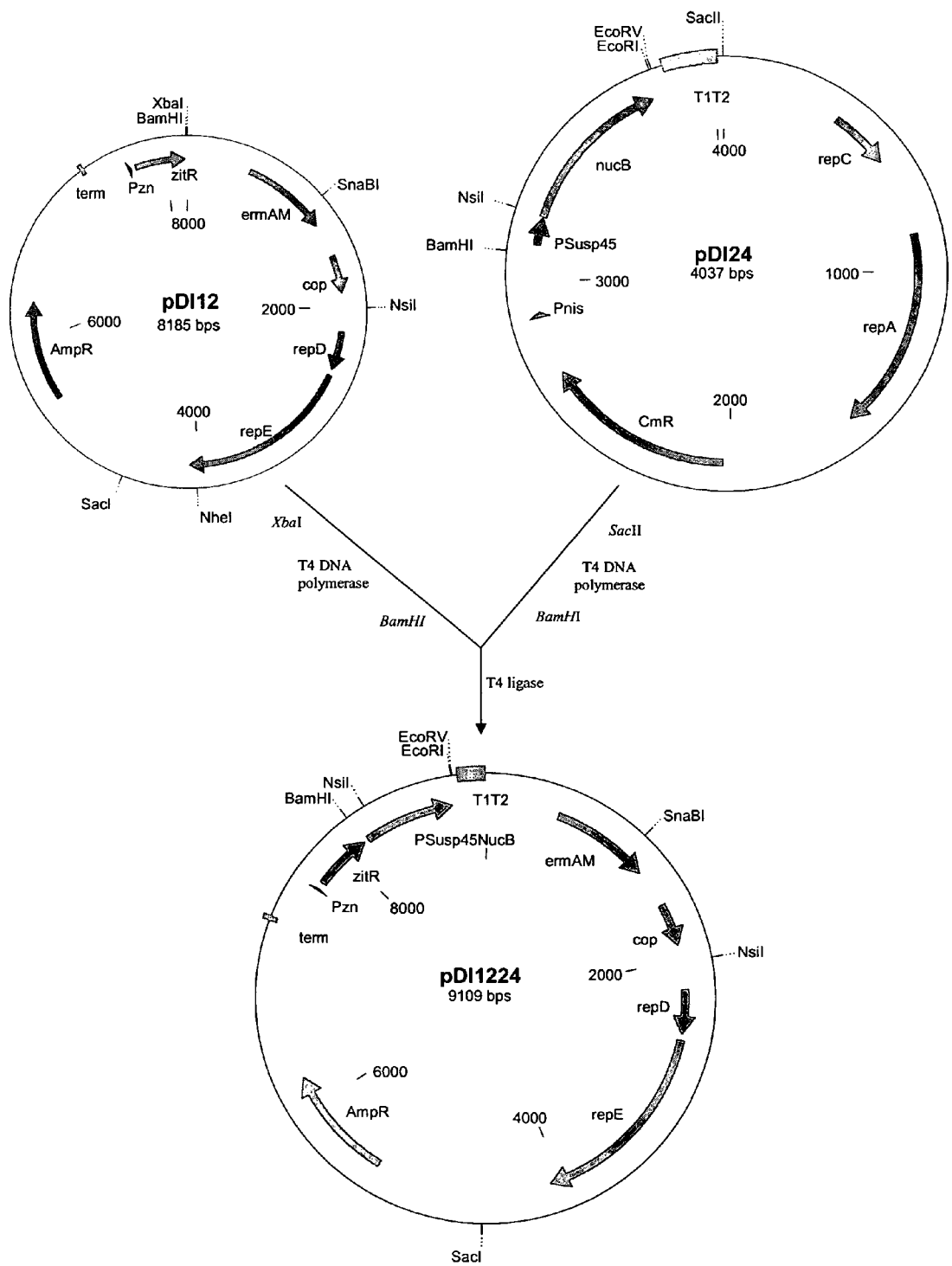
FIG. 5 illustrates the steps involved in constructing plasmid pDI1224 from plasmids pDI12 and pDI24.

The steps for constructing pDI1224 are represented in FIG. 5.

Figure 6:
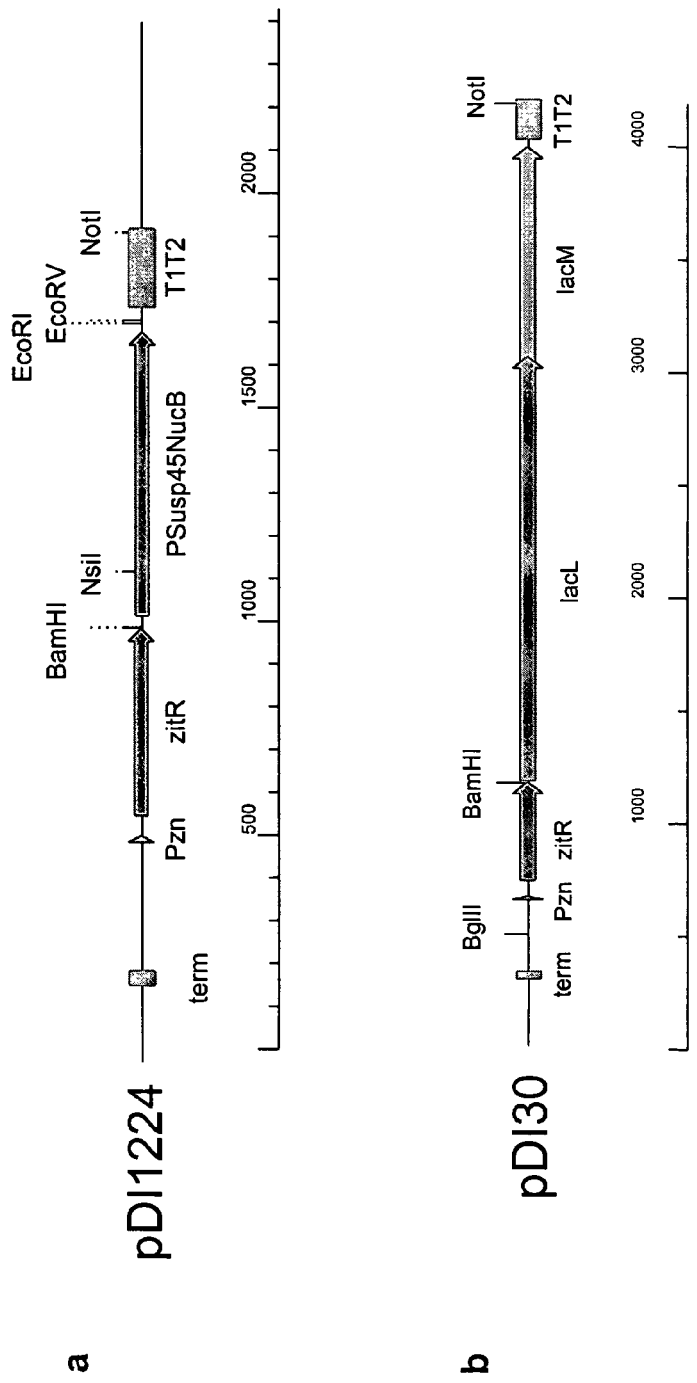
FIG. 6(a) illustrates a diagram of plasmid pDI1224 containing the reporter gene encoding NucB, under the control of the $p_{Zn}$-ZitR expression system.
FIG. 6(b) illustrates a diagram of plasmid pDI30 containing the lacLM operon encoding P-galactosidose under the control of the $p_{Zn}$-zitR expression system.

The insert of this plasmid containing the reporter gene encoding NucB, under the control of the $p_{Zn}$-zitR expression system, is shown diagrammatically in FIG. 6a.

Plasmid pDI30

In order to quantify the level of expression controlled by $p_{Zn}$ zitR as a function of the environmental $Zn^{2+}$ conditions, another reporter for cytoplasmic localization was used: β-galactosidase from *Leuconostoc mesenteroides* subsp. *cremoris*, encoded by the lacLM operon.

The lacLM operon was amplified by PCR from the plasmid pAMJ769 (MADSEN et al., Mol. Microbiol. 32, 75-87, 1999), using the following pair of primers:

```
LAC5:                                    (SEQ ID NO: 15)
5'-CGCGGATCCTTTGAAAGGATATTCCTC-3'

LAC3:                                    (SEQ ID NO: 16)
5'-CCTACGTATTAGAAATGAATGTTAAAGC-3'.
```

The primers LAC5 and LAC3 were, respectively, designed according to the sequence of the plasmid pAK80, published by ISRAELSEN et al., (*Appl. Environ. Microbiol.* 61, 2540-2547, 1995) and according to the sequence of the lacLM genes available on GeneBank under the number M92281. LAC5 overlaps the potential ribosome binding site of lacL (RBS, indicated in bold on the sequence), and LAC3 contains the stop codon of lacM. In addition, in order to make it possible to clone the PCR fragment, the BamHI and SnaBI restriction sites were introduced at the ends of LAC5 and LAC3, respectively (underlined on the sequences). In order to construct pDI30, the recipient plasmid pDI1224 was digested with BamHI and EcoRV so as to delete the secreted reporter PSusp45NucB, and the lacLM PCR product, after digestion with BamHI and SnaBI, was inserted in its place. This ligation mixture was used to transform the *L. lactis* strain MG1363. The transformants were selected in M17 agar medium+0.5% glucose+5 µg/ml erythromycin+160 µg/ml X-Gal (5-bromo-4-chloro-3-indolyl-β-D-galactoside)+0.5 mM EDTA. The addition of X-Gal and of EDTA to the medium makes it possible to screen the clones which carry pDI30 for their blue phenotype, associated with hydrolysis of the X-Gal by the β-galactosidase (it was verified that, in the absence of EDTA, the clones remain white, which indicates that the medium contains sufficient $Zn^{2+}$ to shut down the expression of LacLM).

The insert of this plasmid containing the lacLM operon encoding β-galactosidase, under the control of the $p_{Zn}$-zitR expression system, is shown diagrammatically in FIG. 6b.

Figure 7:
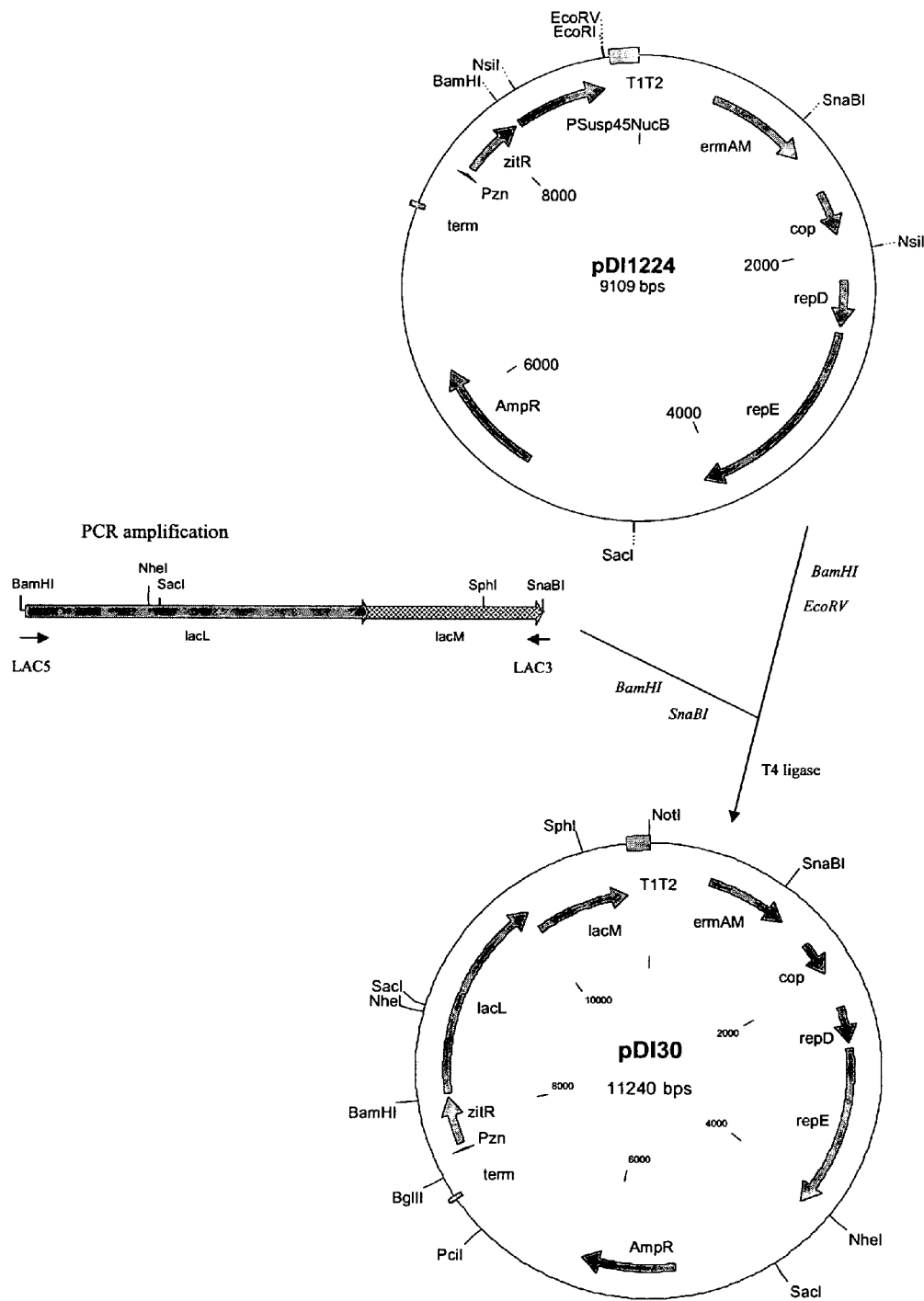
FIG. 7 illustrates the steps involved in constructing plasmid pDI30.

The steps for constructing pDI30 are represented in FIG. 7.

Example 3

Quantification of the Level of Induction of a Cytoplasmic Localization Reporter Gene Under the Control of the $p_{Zn}$zitR Promoter The *L. lactis* strain MG1363 carrying the plasmid pDI30 was cultured in chemically defined SA medium, supplemented with 1 µM $Zn^{2+}$. Growth was effected overnight at 30° C. without shaking.

The following day, the culture was diluted to approximately 1/100th in SA medium (which contains $ZnSO_4$ at the concentration of 10 nM) and the growth was monitored by measuring the $OD_{600}$. At the value $OD_{600}$~0.2, the culture was divided up into several subcultures subjected to various treatments: no addition or addition of EDTA at concentrations of 10-30-50-100-300 or 500 µM, or alternatively addition of $Zn^{2+}$ at a concentration of 1 µM. At various treatment times, the growth was monitored by measuring the $OD_{600}$, and the β-galactosidase (β-Gal) activity of the bacterial extracts was quantified by the Miller method. In the presence of ONPG, β-Gal produces yellow-colored O-nitrophenol which can be assayed by measuring the optical density at 420 nm; 1 Miller unit of β-Gal activity is defined as producing 1 nmol of O-nitrophenol per minute per unit of optical density per ml of culture.

Figure 8:
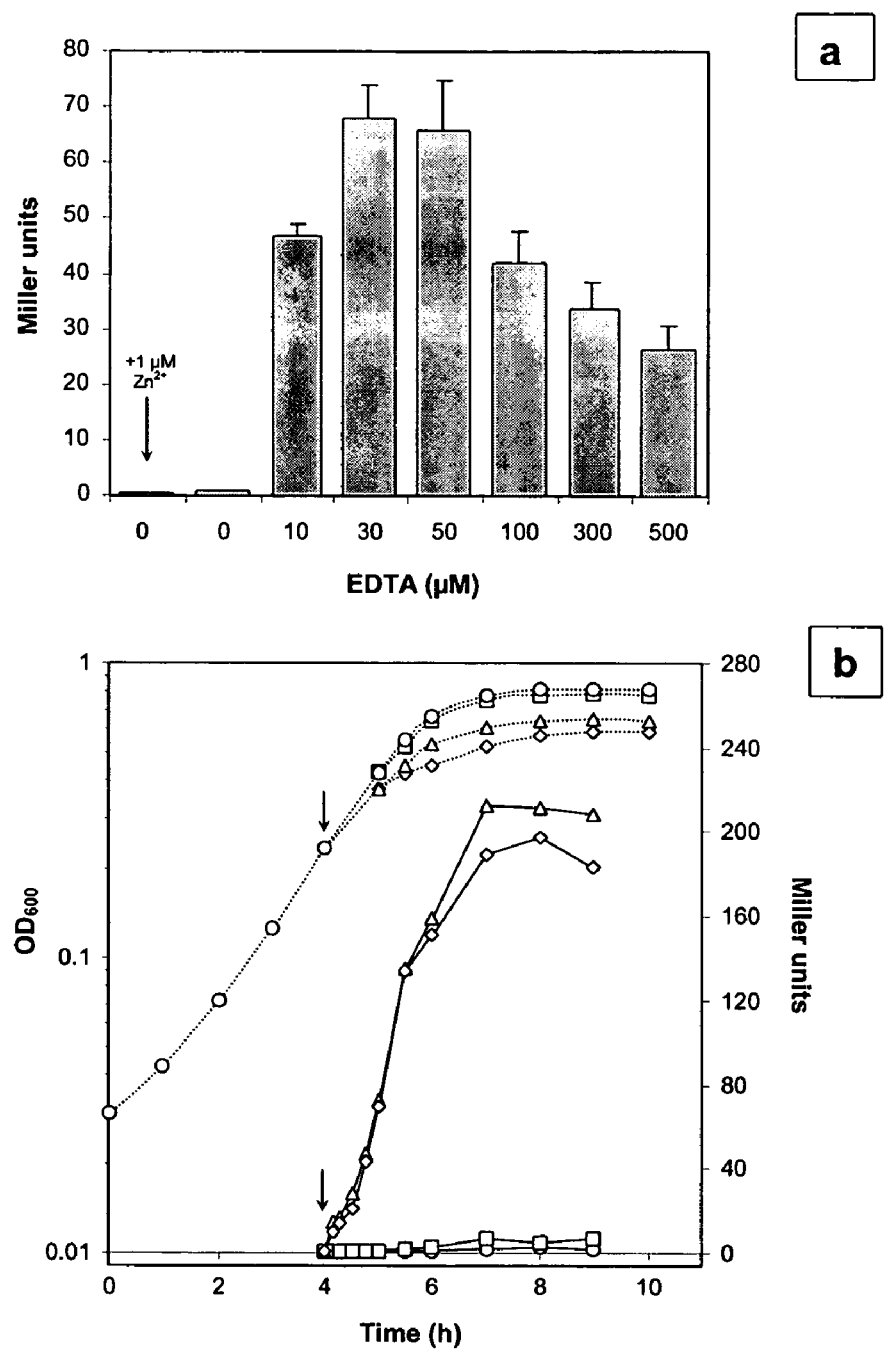
FIG. 8(a) illustrates β-Gal activity of bacterial extracts measured after 1 hr of treatment as a function of EDTA added (expressed in μM).
FIG. 8(b) illustrates growth curves (as dotted lines) and β-Gal activity (as solid lines) for certain subcultures measured as a fraction of time.

The β-Gal activity measured after 1 h of treatment, as a function of the concentration of EDTA added (expressed in µm), is represented in FIG. 8a; the subculture supplemented with $Zn^{2+}$ at 1 µM is indicated with an arrow (+1 µM Zn).

In the absence of EDTA or in the presence of $Zn^{2+}$ a very low basal level of β-Gal activity is observed. In the presence of EDTA, a very clear induction of the β-Gal activity is observed, which depends on the concentration of EDTA: the maximum level of activity (induction by a factor >100) is obtained for the concentrations of 30 µM or 50 µM of EDTA, which therefore defines the optimal concentration range to be used under these conditions in order to have maximum induction.

In the course of the same experiment, the growth (curves as dotted lines) and the β-Gal activity (curves as solid lines) of certain subcultures were also measured as a function of time; the results are represented in FIG. 8b. The subcultures studied were subjected to, at $OD_{600}$~0.2 (indicated by an arrow), the following treatments: no addition (□); addition of 30 µM EDTA (Δ) or 50 µM EDTA (◇); addition of 1 µM $Zn^{2+}$ (○). At regular time intervals after these treatments, aliquots were taken in order to quantify the β-Gal activity of the bacterial cells. The level of induction depends both on the time of exposure to EDTA and on its concentration. The maximum induction is by a factor >500 for 3 to 4 h in the presence of 30 µM EDTA, which makes it possible to define the conditions for using the system.

Example 4

Construction of Plasmids Containing a Sequence Encoding a Secretion Signal Peptide These plasmids are constructed by substitution of elements of the PSUsp45 secretion system of the plasmid pSEC with those of the Exp4 secretion system.

The sequence encoding the Exp4 signal peptide (PSExp4), accompanied by the Exp4 translation signals, i.e. its RBS (or RBSExp4) and its translation initiation codon, was amplified from the plasmid pVE8022 (POQUET et al., 1998, mentioned above), using the pairs of primers Exp4-5+Exp4-NdeI and M13reverse+Exp4-NdeI, the sequences of which are:

```
M13reverse:                              (SEQ ID NO: 11)
5'-CAGGAAACAGCTATGACC-3';

Exp4-5:                                  (SEQ ID NO: 12)
5'-GTTCTAAGGATCCATTAACTTAAGGAG-3';

Exp4-NdeI:                               (SEQ ID NO: 13)
5'-TTTGTGATGCATATGCAAATACAACGGCTGTTG-3'.
```

The primers Exp4-5 and Exp4-NdeI were designed based on the 5' portion of the exp4 gene of the *L. lactis* strain MG1363 (GENBANK number U95836).

In Exp4-5 and Exp4-NdeI, restriction sites (in bold) are introduced at the ends of PSExp4 in order to facilitate its cloning, respectively BamHI in the 5' position and NsiI in the 3' position (downstream of the potential cleavage site of PSExp4). The NsiI site is introduced at a position which makes it possible to clone PSExp4 in phase with NucB.

Moreover, Exp4-NdeI comprises an NdeI site (underlined) so as to allow possible cloning (of a protein of interest) in phase with PSExp4. Insertion of the NdeI and NsiI sites introduces only two amino acids at the N-terminal end of NucB: Tyr (encoded by TAT in Exp4-NdeI) and Ala (GCA in Exp4-NdeI), which causes little disturbance of the sequence.

Amplification with Exp4-5+Exp4-NdeI using the DNA of the plasmid pVE8022 produces a 117 by fragment.

The peptide encoded by this fragment corresponds to the sequence MKKINLALLTLATLMGVSSTAVVFA↓YA (SEQ ID NO:14) which corresponds to the sequence of the Exp4 signal peptide, up to the predicted cleavage site (indicated with an arrow) followed by the two amino acids Y and A inserted upstream of NucB.

After digestion with BamHI and NsiI, the 117 by Exp4-5+ Exp4-NdeI fragment is inserted by ligation into pSEC1 (CHATEL et al., 2001, mentioned above) digested with the same enzymes, which allows the substitution of PSUsp45 with PSExp4.

PCR amplification with M13reverse Exp4-NdeI using the DNA of the plasmid pVE8022 produces a 799 by fragment. This fragment contains the Exp4 transcription, translation and secretion signals.

After digestion with EcoRV and NsiI, this fragment is inserted into pSEC1 digested beforehand with XbaI, treated with T4 phage polymerase, and digested with NsiI. In the resulting plasmid, the production and the secretion of NucB are thus placed under the control of the Exp4 transcription, translation and secretion signals.

The invention claimed is:

1. An expression cassette comprising:
   a) a bacterial promoter, $p_{Zn}$, comprising a binding site for the *Lactococcus lactis* ZitR protein, which site comprises the following sequence:

AAAAATAANGTNNNNNNNNTTGACATTATTTTT, (SEQ ID NO: 1)

in which TTGACA is the −35 box of said promoter, and N represents A, C, G or T; and
   b) a sequence encoding a *Lactococcus* ZitR polypeptide, said polypeptide having at least 85% identity with the *Lactococcus lactis* ZitR protein encoded by nucleotides 357-794 of SEQ ID NO: 9
   c) a sequence containing at least one restriction site for inserting a nucleotide sequence of interest;
   wherein said sequences b) and c) are under transcriptional control of the promoter, $p_{Zn}$, and wherein said expression cassette does not comprise any part of the ZitS coding sequence.

2. The expression cassette of claim 1, wherein the $p_{Zn}$ ZitR binding site comprises the following sequence:

AAAAATAANGTNNNNNNNNTTGACATTATTTTTNNNNNNNNNNTATAAT. (SEQ ID NO: 2)

3. The expression cassette of claim 2, wherein the $p_{Zn}$ promoter ZitR binding site comprises a sequence selected from the group consisting of:

AAAAATAATGTTAACTGGTTGACATTATTTTTACTTTGCTATATAATT (SEQ ID NO: 4)
   AACCAGTA; and

AAAAATAACGTTAACTGGTTGACATTATTTTTCTTTGCTATATAATTA (SEQ ID NO: 5)
   ACCAGTA.

4. The expression cassette of claim 1, wherein sequence c) comprises a nucleotide sequence encoding an extracellular targeting peptide, and the at least one restriction site is for cloning of a nucleotide sequence encoding a peptide of interest as a translational fusion with said targeting peptide.

5. The expression cassette of claim 4, wherein said extracellular targeting peptide comprises the following sequence:

MKKINLALLTLATLMGVSSTAVVFA. (SEQ ID NO: 6)

6. The expression cassette of claim 1, wherein sequence c) comprises a nucleotide sequence of interest inserted at the at least one restriction site.

7. A recombinant vector comprising the expression cassette of claim 1.

8. A gram-positive bacterium transformed with the expression cassette of claim 1.

9. The bacterium of claim 8, which is a lactic acid bacterium.

10. The expression cassette of claim 1, wherein the polypeptide of b) has at least 95% identity with the *Lactococcus lactis* ZitR protein encoded by nucleotides 357-794 of SEQ ID NO: 9.

11. An expression cassette, comprising:
    a) a bacterial promoter $p_{Zn}$, comprising a binding site for the *Lactococcus lactis*-ZitR protein, which site comprises the following sequence:

AAAAATAANGTNNNNNNNNTTGACATTATTTTT (SEQ ID NO: 1)

in which TTGACA is the −35 box of said promoter, and N represents A, C, G or T; and
    b) at least one restriction site allowing the insertion of a nucleotide sequence under the transcriptional control of said promoter, and wherein the expression cassette does not comprise any part of the ZitS coding sequence.

* * * * *